(12) United States Patent
Varanguien De Villepin

(10) Patent No.: US 9,581,544 B2
(45) Date of Patent: Feb. 28, 2017

(54) APPARATUS FOR ANALYZING PHASES OF MULTIPHASE MIXTURES

(71) Applicant: FORMULACTION, L'Union (FR)

(72) Inventor: Ronan Varanguien De Villepin, Endoufielle (FR)

(73) Assignee: FORMULACTION, L'Union (FR)

( * ) Notice: Subject to any disclaimer, the term of this patent is extended or adjusted under 35 U.S.C. 154(b) by 0 days.

(21) Appl. No.: 14/774,087

(22) PCT Filed: Mar. 4, 2014

(86) PCT No.: PCT/FR2014/050483
§ 371 (c)(1),
(2) Date: Sep. 9, 2015

(87) PCT Pub. No.: WO2014/140451
PCT Pub. Date: Sep. 18, 2014

(65) Prior Publication Data
US 2016/0018322 A1    Jan. 21, 2016

(30) Foreign Application Priority Data
Mar. 12, 2013    (FR) ...................................... 13 52187

(51) Int. Cl.
*G01N 21/25* (2006.01)
*G01N 21/17* (2006.01)
(Continued)

(52) U.S. Cl.
CPC ......... *G01N 21/359* (2013.01); *G01N 21/253* (2013.01); *G01N 21/51* (2013.01);
(Continued)

(58) Field of Classification Search
CPC ... G01N 2021/0357; G01N 2021/0367; G01N 2021/4709; G01N 21/253;
(Continued)

(56) References Cited

U.S. PATENT DOCUMENTS 5,170,662 A * 12/1992 Brault .................... G01L 5/133
73/112.04
5,783,826 A    7/1998 Meunier
(Continued)

FOREIGN PATENT DOCUMENTS

EP    0760092 B1    2/1998
EP    2144051 A1    1/2010
(Continued)

*Primary Examiner* — Jennifer Wecker
(74) *Attorney, Agent, or Firm* — Volpe and Koenig, P.C.

(57) ABSTRACT

The invention relates to an apparatus comprising: a measuring head (10) having a slot (18) for receiving a measurement cell (26) and means (28) for emitting electromagnetic radiation, and means (32, 36) for detecting radiation from said emission means (28) after it has passed through the measurement cell (26); means (16) for translatably driving and means (12, 14) for translatably guiding, allowing the substantially vertical longitudinal movement of the measurement head (10); at least two recesses (44) each intended for receiving a measurement cell (26) and arranged one above the other in a longitudinal direction, the recesses (44) as well as the driving means (16) and the guiding means (12, 14) being configured such that during the translational movement of the measurement head (10) along the nominal travel thereof each recess is placed inside the slot (18) of the measurement head (10).

16 Claims, 5 Drawing Sheets

(51) Int. Cl.
*G01F 1/00* (2006.01)
*G01N 21/359* (2014.01)
*G01N 21/51* (2006.01)
*G01N 35/00* (2006.01)
*G01N 21/27* (2006.01)
*G01F 23/292* (2006.01)
*G01N 21/47* (2006.01)
*G01N 21/55* (2014.01)
*G01N 21/03* (2006.01)

(52) U.S. Cl.
CPC ..... *G01N 35/00029* (2013.01); *G01F 23/292* (2013.01); *G01F 23/2928* (2013.01); *G01N 21/255* (2013.01); *G01N 21/474* (2013.01); *G01N 21/55* (2013.01); *G01N 2021/0357* (2013.01); *G01N 2021/0367* (2013.01); *G01N 2021/4709* (2013.01); *G01N 2201/0438* (2013.01); *G01N 2201/101* (2013.01)

(58) Field of Classification Search
CPC ................ G01N 21/359; G01N 21/51; G01N 2201/0438; G01N 2201/101; G01N 35/00029
See application file for complete search history.

(56) References Cited

U.S. PATENT DOCUMENTS

| | | | |
|---|---|---|---|
| 6,388,751 B1* | 5/2002 | Holley | G01N 21/253 356/436 |
| 2006/0228734 A1* | 10/2006 | Vann | B01L 3/5025 435/6.19 |
| 2010/0007891 A1* | 1/2010 | Carroll | G01N 21/51 356/440 |
| 2011/0228272 A1 | 9/2011 | Brunel | |
| 2013/0008514 A1* | 1/2013 | Enomura | B01F 3/0807 137/1 |
| 2013/0130369 A1* | 5/2013 | Wilson | B01L 3/5085 435/289.1 |
| 2014/0110105 A1* | 4/2014 | Jones | E21B 47/10 166/250.01 |

FOREIGN PATENT DOCUMENTS

FR 2453405 A1 10/1980
FR 2938917 A1 5/2010

\* cited by examiner

APPARATUS FOR ANALYZING PHASES OF MULTIPHASE MIXTURES

FIELD OF THE INVENTION

The present invention relates to an apparatus for analyzing phases of multiphase mixtures.

BACKGROUND

Such an analysis apparatus is intended in particular for detecting and measuring incipient phenomena of phase separation, sedimentation in particular into various mixtures. The mixtures concerned are mixtures in which singularities or discontinuities (liquid, solid or gaseous, or a combination) are dispersed in a continuous medium of a different composition and/or state. For example, this concerns emulsions if two or more liquid phases are mixed or suspensions if solid particles are dispersed in a liquid. There are numerous fields of application for such an apparatus. The chemical and para-chemical industries are the main fields, but such devices can be used in any field where it is necessary to analyze the structure and/or stability of a multiphase mixture.

Document EP-0,760,092 discloses an apparatus for performing an analysis of a sample of a multiphase mixture. The method described therein and the corresponding device allow conducting an optical analysis of a mixture and are ideal for characterizing the stability of a mixture, for example a concentrated liquid dispersion.

The method described in that document of the prior art consists of emitting a light beam through a sample of the multiphase mixture and measuring the light that is backscattered and potentially transmitted all along the height of the sample. In this manner, it is possible to detect variations in size (coalescence, flocculation) and phase separations (sedimentation, creaming) of the mixture analyzed.

Systems that use this method currently only permit analysis of a single sample. There are "loaders" of course, which manipulate samples stored in a storage unit, preferably temperature regulated, to bring them one after another to the associated analysis device. The main drawback of this combination of analysis device and loader is related to sample transport. The transport act has some impact, even if carried out carefully, and may for example lead to dispersions in areas where the destabilization phenomenon is more visible and thus mask the phenomenon of interest. Another drawback is the cost of the loader, because it must be precise and carry the samples with very little shaking. In addition, its price increases rapidly with the number of samples to be handled.

Also known from documents U.S. Pat. No. 6,388,751 and FR-2 453 405 are devices for analyzing a plurality of samples placed in tubes. Several tubes are arranged in a vertical position next to one another and an analysis head moves horizontally in front of each of the tubes in order to obtain a measurement at a given height. These devices are not suitable for phase analysis of a multiphase mixture.

Document EP-2 144 051 provides a storage rack adapted for an analysis device. The rack is designed to hold tubes each containing a sample and arranged vertically. A reading head is moved on an arm in two horizontal directions, and in one vertical direction. The reading head here has three degrees of freedom. Aside from the complexity of this device, it is difficult to ensure precise positioning of the sample relative to the reading head, and in the case of phase analysis of a multiphase mixture, to obtain repeatability in the measurement results.

SUMMARY

The present invention therefore aims to provide an apparatus for analyzing phases of a multiphase mixture which allows reliable analysis of multiple samples. Advantageously, the analysis apparatus will provide the same analysis result for a sample regardless of its position in the apparatus. Preferably, the cost of this device will be competitive with existing devices.

To this end, the present invention provides an apparatus for analyzing a phase of multiphase mixtures, comprising:
  a measurement head having on the one hand a recess for receiving a measurement cell containing a mixture to be analyzed, and on the other hand means for emitting electromagnetic radiation and means for detecting electromagnetic radiation coming from said emission means and potentially having entered the measurement cell, and
  means for driving and guiding in translation, for moving the measurement head along a nominal path in a direction referred to as a substantially vertical longitudinal direction.

According to the invention, said apparatus further comprises at least two casings each intended for receiving a measurement cell and arranged one above the other in the longitudinal direction, and
  the casings as well as the driving and guiding means are configured such that, during the translational movement of the measurement head along its nominal path, each casing is placed inside the recess of the measurement head.

It is therefore proposed that the samples be arranged on top of one another in a novel manner for the analysis. The longitudinal direction is therefore substantially vertical here.

To ensure proper guidance of the measurement head, it is proposed that the driving and guiding means comprise a linear ball bearing slide rail. In this embodiment, the linear ball bearing slide rail advantageously is placed at the bottom of the recess of the measurement head. This positioning makes it possible to have a compact structure while providing good guidance.

For proper positioning of a measurement cell with respect to the measurement head, it is proposed that the apparatus for analyzing phases comprises a support rail having bearing surfaces for receiving an external face of a measurement cell. To improve the precision of this positioning, the bearing surfaces are advantageously arranged in a dihedral angle.

One embodiment provides that each casing is associated with a cell holder with apertures, this holder being intended for receiving a measurement cell. In this embodiment, the apparatus for analyzing phases may further comprise elastic means which bias each cell contained in a holder toward the bottom of the recess of the measurement head. It is thus possible to guarantee near-perfect positioning of the cell in the apparatus.

An embodiment which contributes to achieving proper positioning of a measurement cell in the apparatus for measuring phases provides that each casing is associated with an access door mounted so as to pivot about an axis parallel to the longitudinal direction, each door having a face carrying a cell holder arranged such that when in a pivoted position, referred to as the closed position, the cell holder is in place in the corresponding casing.

BRIEF DESCRIPTION OF THE DRAWINGS

Details and advantages of the invention will be more apparent from the following description, provided with reference to the accompanying drawings in which.

DETAILED DESCRIPTION OF THE PREFERRED EMBODIMENTS

Figure 1:
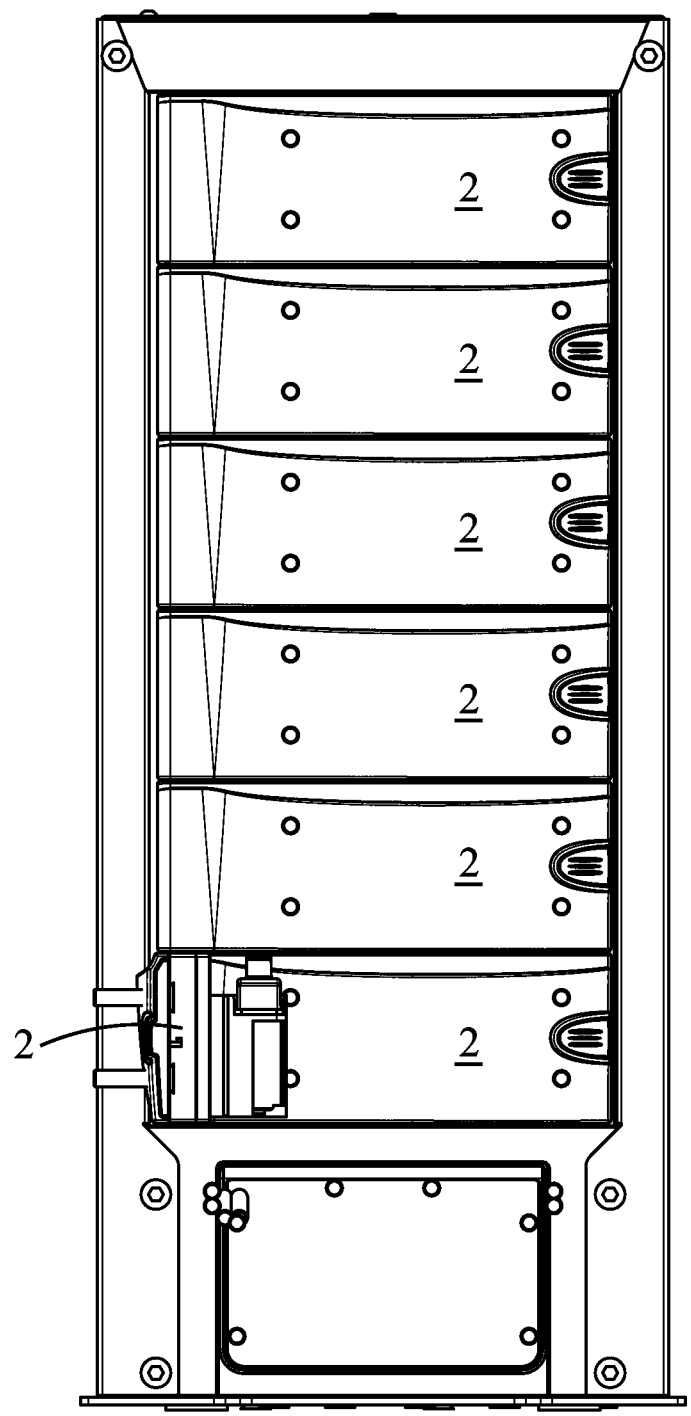
FIG. 1 is an elevational view of a sample analysis device according to the invention.

FIG. 1 illustrates an analysis device adapted to enable analysis of six samples, in particular samples of multiphase mixtures. This embodiment is given by way of non-limiting example, and those skilled in the art will understand from the following description that an analysis device can be provided for measuring a different number of samples.

FIG. 1 illustrates a possible external appearance of a sample analysis device. This device comprises an inner structure supporting the actual analysis device and an outer casing visible in FIG. 1. One will note in this FIG. 1 the presence of six doors 2 which will be described in more detail below. One of the doors 2 is shown in the open position and in the closed position.

As one can see in this front view, the doors 2 have an elongated rectangular shape. For the remainder of this description, the following orientation will be used: the longitudinal edges of the doors 2, corresponding to the long sides of the rectangles, extend horizontally, and the doors are arranged one above the other in a substantially vertical plane.

Figure 2:
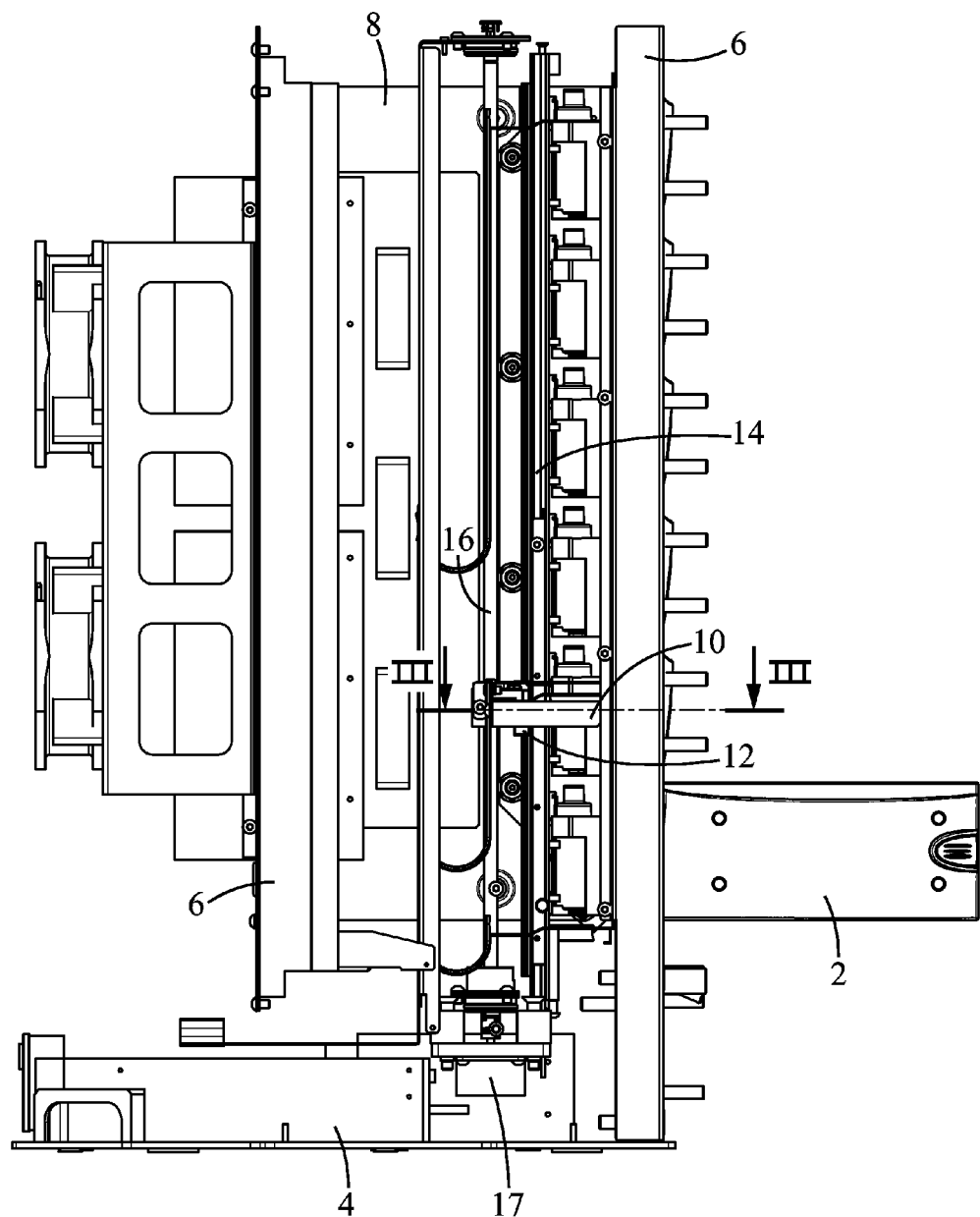
FIG. 2 is a side view of the device of FIG. 1, the protective elements having been hidden to expose the device.

FIG. 2 is a side view corresponding to the front view of FIG. 1 but after removal of the external casing to allow viewing the components inside the analysis device to be described.

Visible in this figure are a base 4, and a frame with vertical uprights 6 and crosspieces 8. The frame serves to support the means for driving and guiding a measurement head 10 in translation. Guidance of said head is provided by a linear ball bearing slide rail which comprises a carriage 12 and a guide rail 14. The measurement head 10 is driven by means of a lead screw 16 driven in rotation by a motor 17 (FIG. 2) mounted in the base 4.

Figure 3:
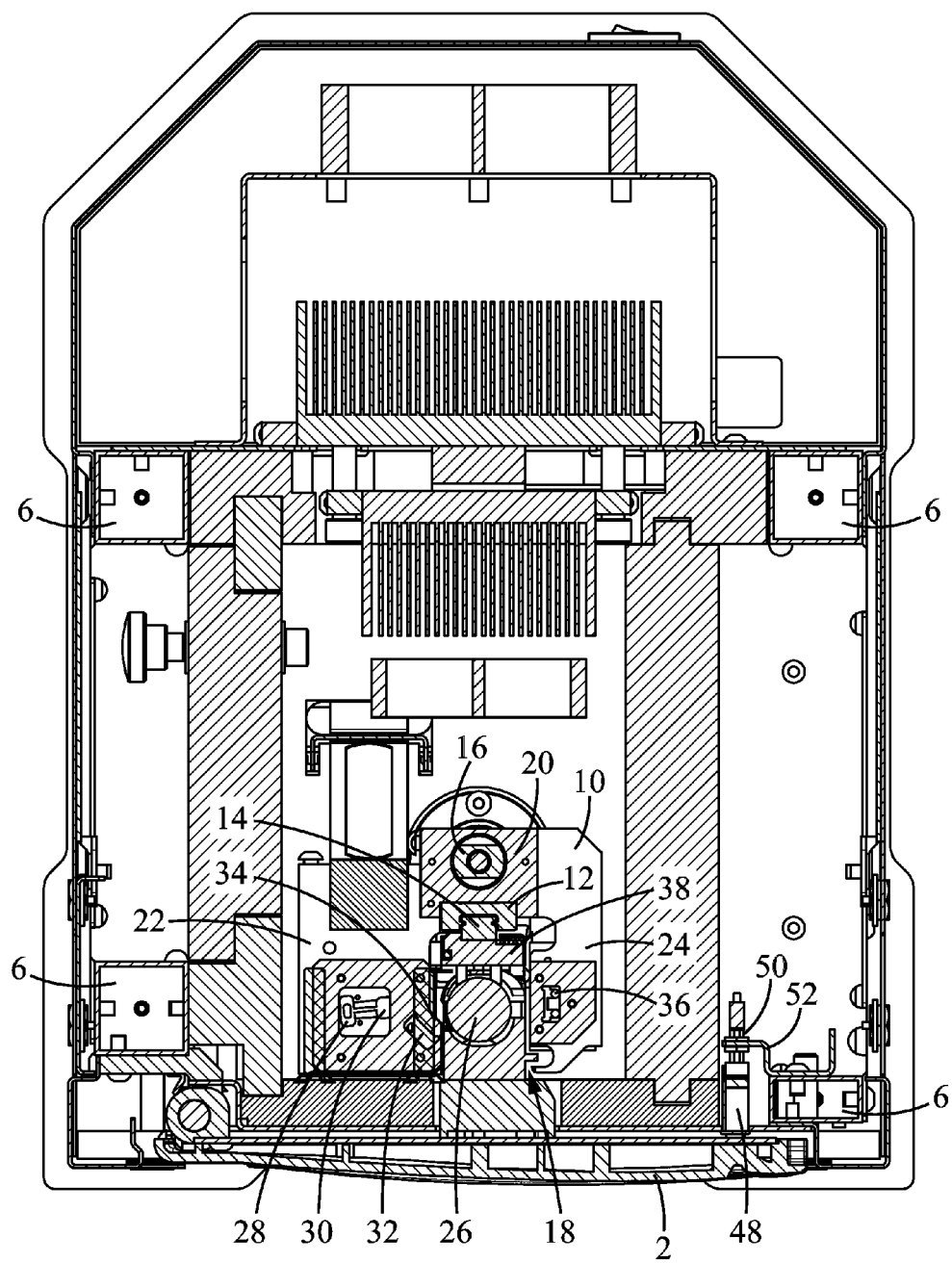
FIG. 3 is a partial cross-sectional view of a sample analysis device along section line III-III of FIG. 2.

FIG. 3, which is a sectional view, provides a better understanding of the relative positions of these elements. In the center of this figure is the measurement head 10. The measurement head 10 corresponds to the movable holder (denoted with a 2 in patent EP-0 760 092B1) and to the elements it carries. This element is adapted in its shape which is generally rectangular and elongated, providing a recess 18 which extends transversely and is relatively wide. Thus, in a top view which also corresponding to the view of FIG. 3, the measurement head 10 has a U-shape with a base 20, a first arm 22, and a second arm 24. The recess 18 corresponds to the space between the two arms of the measurement head. It is intended to accommodate a measurement cell 26 containing a multiphase mixture to be analyzed, as illustrated in FIG. 3.

Technically, measurement head 10 is a measurement head with the characteristics of the measurement head described in EP-0 760 092 but of a shape adapted to the environment described herein. Thus, measurement head 10 comprises means for emitting electromagnetic radiation toward the measurement cell 26 and means for detecting electromagnetic radiation backscattered by a mixture located within the measurement cell 26. Advantageously and as illustrated in FIG. 3, it further comprises means for detecting electromagnetic radiation transmitted by the mixture in the measurement cell 26.

The means for emitting electromagnetic radiation comprise, for example, a diode 28 which emits in the near infrared. In the embodiment of FIG. 3, the diode 28 is carried by the first arm 22 of the measurement device. As a non-limiting illustration, the diode 28 emits rays having a wavelength of 880 nm (880 $10^{-9}$ m). The radiation emitted by the diode 28 first passes through a rectilinear slit 30 so that the mixture in the measurement cell 26 is irradiated along a horizontal plane.

Electromagnetic radiation backscattered by the mixture contained in the measurement cell can be detected by a photodiode 32. In the illustrative case of FIG. 3, the photodiode 32 is carried by the first arm 22 of the measurement cell and is located near the emission diode 28. It receives the backscattered radiation after the latter has passed through a slit 34.

Electromagnetic radiation transmitted through the mixture contained in the measurement cell can be detected by a photodiode 36. In the illustrative case of FIG. 3, the photodiode 36 is carried by the second arm 24 of the measurement cell and is directly facing diode 28 in the emission direction of said diode 28.

Reference is made here to the description in patent EP-0 760 092B1, particularly columns 4 and 5, concerning further details of an embodiment of a measurement head which can be used in the present invention. Of course, this is an example of a preferred embodiment and the numerical values given are not limiting.

To obtain a measurement, a measurement cell 26 is placed within the recess 18 of the measurement head. The measurement cell should be properly positioned relative to the emission diode 28, to the photodiode 32 for detecting scattered radiation, and to the photodiode 36 for detecting transmitted radiation. FIGS. 2 to 5 propose a non-limiting example arrangement which allows proper mechanical positioning of the measurement cell 26 with respect to the measurement head 10. A support rail 38 extends vertically as a backbone of the device. It provides a face, called the front face, which a measurement cell 26 abuts against when carrying out a measurement. This front face is oriented towards the opening of the recess 18 of the measurement head 10. On the opposite side, in other words facing the bottom of the recess 18, the support rail 38 supports the guide rail 14. The latter cooperates with a carriage 12 which is slidable, by means of ball bearings, on the guide rail 14. The carriage 12 carries the measurement head 10 and is arranged at the bottom of the recess 18 of this measurement head. The lead screw 16 passes through the base 20 of the measurement head 10 and thus drives the measurement head 10 in translation along the support rail 38 via the carriage 12 on one side and the guide rail 14 on the other.

The following description relates to measurement cells 26 which each have the general shape of a right circular cylindrical tube (in the region where analysis of a mixture is to be carried out), but other measurement cell shapes could be considered, such as a tubular cylinder of square cross-section. These measurement cells 26 are arranged one above the other and in the extension of one another. The longitudinal axes corresponding to these measurement cells (longitudinal axis defined by the cylindrical shape) are all vertical—and thus parallel to the support rail 38.

The support rail 38 has, on its front face, bearing studs 40 which each have a bearing face 42. The studs 40 are arranged in two vertical columns, the bearing faces 42 of studs in the same column all being coplanar. The bearing faces 42 of the studs 40 of the two columns define a dihedral angle adapted to the dimensions of a measurement cell 26. Preferably, the bearing faces 42 are defined such that when a measurement cell 26 bears against two studs in two separate columns, the bearing faces 42 are tangent to the external surface of the measurement cell. Preferably (as suggested by FIG. 4), a measurement cell 10 bears against four studs 40 (two in each column of studs) during phase analysis of a mixture.

Figure 4:
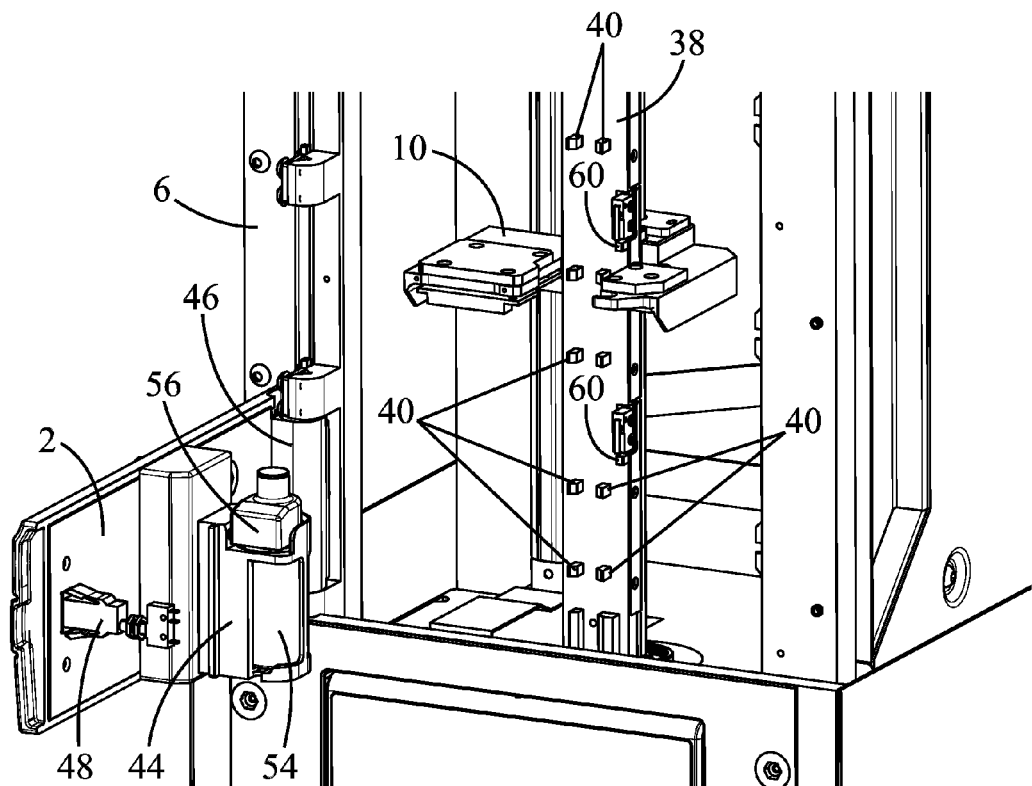
FIG. 4 is a partial perspective view illustrating the introduction of samples into a sample analysis device.
Figure 6:
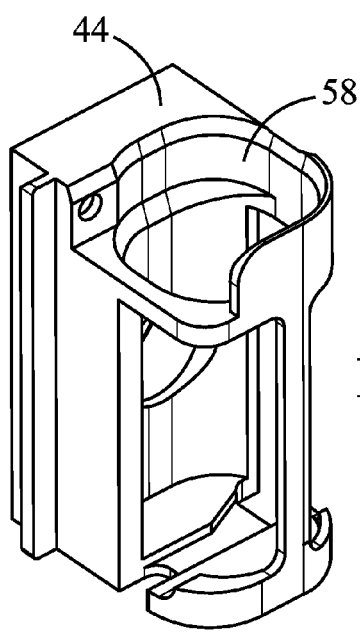
FIG. 6 shows an enlarged perspective view of a sample holder.
Figure 5:
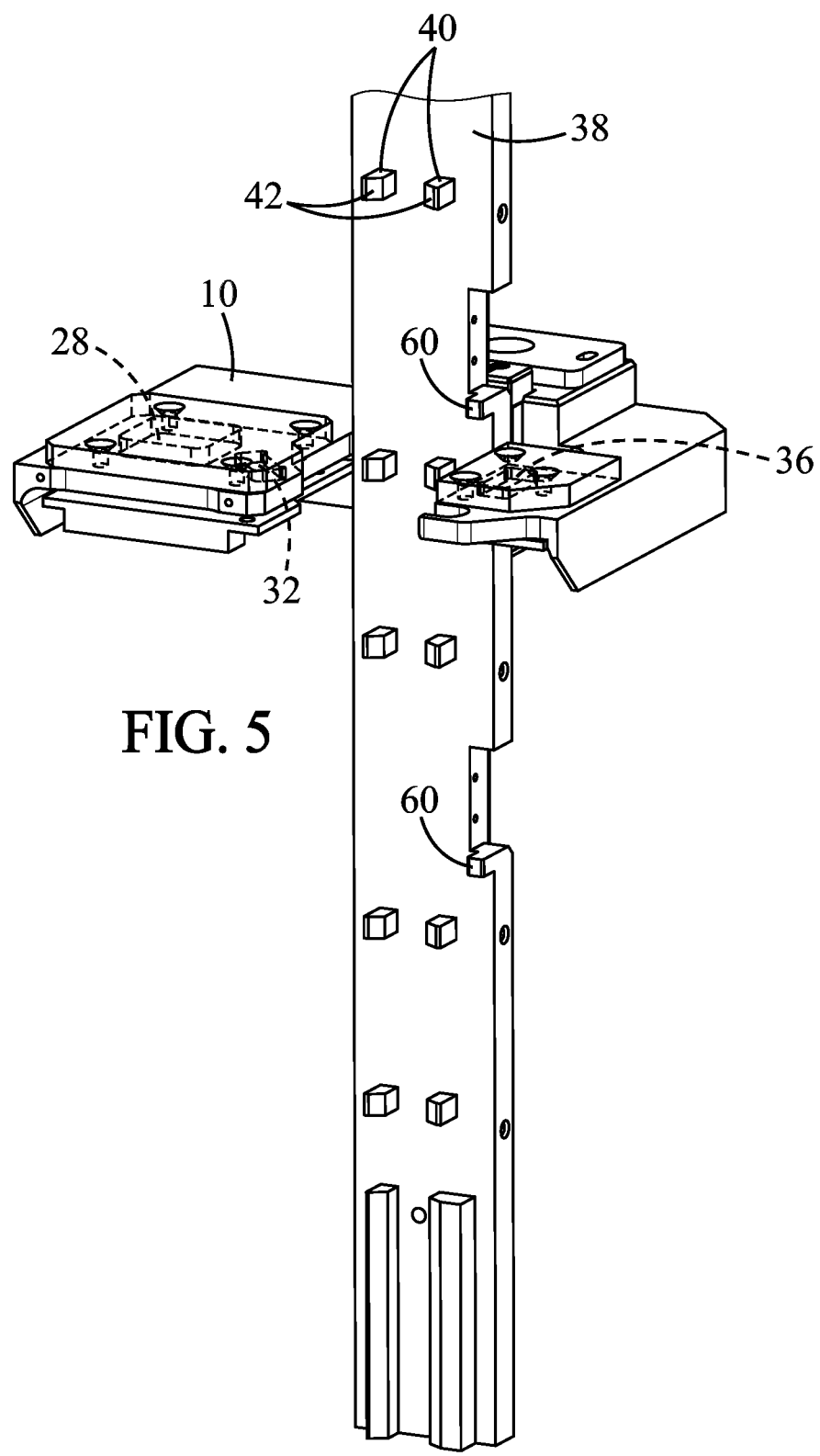
FIG. 5 is a partial perspective view showing sample analysis means.

To position a measurement cell 26 against the support rail 38, said cell is placed in a sample holder 44 (such as the one illustrated in FIG. 6) attached to one side, referred to as the inner side, of a door 2 mentioned above with reference to FIG. 1 and also shown in FIGS. 3 and 4.

Each door 2 has the general shape of an elongated rectangle. It has two long horizontal edges and two (short) transverse edges. One transverse edge is mounted so as to pivot via a hinge 46, directly or indirectly, on a vertical upright 6. The pivot axis of each door 2 is a vertical axis, so that movement of the door 2 occurs in a horizontal plane.

The inner face of each door 2 comprises a sample holder 44 where a measurement cell 26 placed in the sample holder 44 is oriented vertically and can abut against the studs 40 of the support rail 38. As indicated above, it is arranged so that a measurement cell 26 abuts against four studs 40. The sample holder 44 has apertures, so as to allow a measurement cell 26 to abut against the corresponding studs 40 and not form an obstacle to the travel of electromagnetic radiation emitted by the transmission means toward the detection means (photodiode 32 and/or photodiode 36) when the measurement cell 26 is in abutment against the corresponding studs 40 and the measurement head 10 is positioned relative to the measurement cell 26 for performing an analysis of the mixture contained in said measurement cell.

Each door 2 has a closure system for maintaining a measurement cell 26, inserted into its sample holder 44, in abutment against the support rail 38. For this purpose, a hook 48 referred to as a "push-pull" hook is provided near the transverse edge opposite the hinge 46, which cooperates with a hook catch 50 attached to the structure of the device. The hook catch 50 is, for example, mounted on a double-bent member 52 mounted on a vertical upright 6. The closure system comprising the hook 48 and hook catch 50 is preferably provided with a spring to ensure proper positioning of the measurement cell 26 during analysis by eliminating any play due to manufacturing tolerances.

As shown in particular in FIG. 4, a measurement cell 26 has a circular body 54 and a cap 56 that is generally rectangular (in a top view). By offsetting the cap 56 relative to the body 54, a keyway system is achieved by creating in the sample holder 44 a casing 58 of appropriate shape for the cap 56.

A door 2 is opened in order to position a measurement cell 26 in the device. The measurement cell 26 is inserted into the corresponding sample holder 44. The cap 56 of the measurement cell enters its casing 58, thereby pre-positioning the cell. The door 2 can then be closed. The measurement cell 26 rests against the corresponding studs 40. To ensure good repeatable orientation (angular position relative to the axis of symmetry of the body 54 of the measurement cell 26), a reference pin 60 is provided on the support rail 38 such that the cap 56 of the measurement call rests against this pin. In addition, when the cap 56 is resting against the reference pin 60, it is arranged that the body 54 of the measurement cell 26 is only in contact with the sample holder 44 where it rests on the bottom. Thus, the sample holder 44 cannot affect the position of the measurement cell 26 in the device.

The device described above allows positioning up to six samples simultaneously, one above the other. Analysis can be performed once the samples are in place (between one and six samples). By moving the measurement head 10 along the support rail 38, the measurement head 10 passes successively in front of each of the samples placed in the device and thus obtains a series of measurements. Regarding the measurements performed on a sample, we refer again here to patent EP-0 760 092B1, particularly columns 6 and 7 of the description and the method claims in that document.

In the device described above, to perform analyses of six samples (alternative embodiments may provide a device that can house a number of samples not equal to six, either more or less) with a single measurement head, each sample, arranged in a measurement cell, is positioned accurately and reproducibly each time relative to the measurement head.

The device described above provides a path of about 700 mm for a measurement head (for six samples), which can be adapted according to the samples and the number of samples. Precision guidance is provided by the use of a guide rail, preferably a ball bearing slide rail, and by its cooperation with a lead screw to drive the measurement head in translation.

For better positioning of the measurement cell, it is proposed in the above description to have the measurement cell bear against two dihedrals at specific points. This bearing is as localized as possible. In addition, the tube position (angular position relative to its axis of symmetry) is indexed by the abutment of a cap of a specific shape against a reference pin.

With these arrangements, it is possible to achieve excellent performance. Regardless of the operator, a measurement cell will always be similarly positioned in the analysis device. In addition, the measurement cell can be manipulated while maintaining the bottle vertically, without affecting the sample it contains. With such a device, regardless of whether the sample is positioned within the apparatus at a lower, intermediate, or upper "level", the result of the analysis performed with the measurement head will be the same. The position of the sample in the apparatus therefore has no influence on the measurement obtained.

The mechanical structure proposed provides excellent guidance of the measurement head for the entire length of its travel. The guidance system proposed here comprises a limited number of parts for positioning the measurement cell relative to the measurement head.

The invention is not limited to the preferred embodiments described above by way of non-limiting examples. It also relates to variants within the reach of the skilled person, within the scope of the following claims.

What is claimed is:

1. Apparatus for analyzing phases of multiphase mixtures, comprising:
    a measurement head (10) having on the one hand a recess (18) for receiving a measurement cell (26) containing a mixture to be analyzed, and on the other hand means (28) for emitting electromagnetic radiation and means (32, 36) for detecting electromagnetic radiation coming from said transmitting means (28) and potentially having entered the measurement cell (26), and
    a drive mechanism (16) and a guide mechanism (12, 14), configured to, in translation, move the measurement head (10) along a nominal path in a substantially vertical longitudinal direction,
    said apparatus further comprising at least two casings (44) each intended for receiving a measurement cell (26) and arranged one above the other in the longitudinal direction, and
    the casings (44) as well as the drive mechanism (16) and guide mechanism (12, 14) are configured such that, during a translational movement of the measurement head (10) along its nominal path, each casing is placed inside the recess (18) of the measurement head (10).

2. Analysis apparatus according to claim 1, wherein the drive and guide mechanisms (12, 14) comprise a linear ball bearing slide rail.

3. Analysis apparatus according to claim 2, wherein the linear ball bearing slide rail is placed at the bottom of the recess (18) of the measurement head (10).

4. Analysis apparatus according to claim 1, further comprising a support rail (38) having bearing surfaces (42) for receiving an external face of a measurement cell (26).

5. Analysis apparatus according to claim 4, wherein the bearing surfaces (42) are arranged in a dihedral angle.

6. Analysis apparatus according to claim 1, wherein each casing is associated with a cell holder (44) with apertures, said cell holder being intended for receiving a measurement cell (26).

7. Measurement apparatus according to claim 6, comprising elastic means (48, 50) for biasing each cell (26) contained in a holder (44) toward the bottom of the recess (18) of the measurement head (10).

8. Analysis apparatus according to claim 6, wherein each casing (44) is associated with an access door (2) mounted so as to pivot about an axis parallel to the longitudinal direction, wherein each door (2) has a face carrying a cell holder (44) arranged such that when in a pivoted position, referred to as the closed position, the cell holder (44) is in place in the corresponding casing.

9. Method for analyzing phases of multiphase mixtures with a measurement head (10) having on the one hand a recess (18) for receiving a measurement cell (26) containing a mixture to be analyzed, and on the other hand means (28) for emitting electromagnetic radiation and means (32, 36) for detecting electromagnetic radiation coming from said transmitting means (28) and potentially having entered the measurement cell (26), said method comprising:
    a step for driving (16) and guiding (12, 14) in translation, for moving the measurement head (10) along a nominal path in a direction referred to as a substantially vertical longitudinal direction,
    wherein said measurement head (10) moves in front of at least two casings (44) each receiving a measurement cell (26) and arranged one above the other in the longitudinal direction, so that, during a translational movement of the measurement head (10) along its nominal path, each casing comes into the recess (18) of the measurement head (10).

10. Method for analyzing according to claim 9, wherein a linear ball bearing slide rail is used for the driving and guiding of the measurement head.

11. Method for analyzing according to claim 10, wherein the linear ball bearing slide rail is placed at the bottom of the recess (18) of the measurement head (10).

12. Method for analyzing according to claim 9, wherein each measurement cell (26) has an external face lying against bearing surfaces (42) of a support rail (38).

13. Method for analyzing according to claim 12, wherein the bearing surfaces (42) are arranged in a dihedral angle.

14. Method for analyzing according to claim 9, wherein each casing is associated with a cell holder (44) with apertures, said cell holder being intended for receiving a measurement cell (26).

15. Method for analyzing according to claim 14, wherein elastic means (48, 50) are used for biasing each cell (26) contained in a holder (44) toward the bottom of the recess (18) of the measurement head (10).

16. Method for analyzing according to claim 14, wherein each casing (44) is associated with an access door (2) mounted so as to pivot about an axis parallel to the longitudinal direction, wherein each door (2) has a face carrying a cell holder (44) arranged such that when in a pivoted position, referred to as the closed position, the cell holder (44) is in place in the corresponding casing.

* * * * *